United States Patent
Brown et al.

(10) Patent No.: US 7,637,938 B2
(45) Date of Patent: *Dec. 29, 2009

(54) FLEXIBLE STENT

(75) Inventors: Brian J. Brown, Hanover, MN (US);
Timothy J. Ley, Shoreview, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 112 days.

This patent is subject to a terminal disclaimer.

(21) Appl. No.: 11/636,768

(22) Filed: Dec. 11, 2006

(65) Prior Publication Data

US 2007/0106369 A1    May 10, 2007

Related U.S. Application Data

(63) Continuation of application No. 10/160,531, filed on May 31, 2002, now Pat. No. 7,229,470, which is a continuation of application No. 09/426,479, filed on Oct. 26, 1999, now Pat. No. 6,409,753.

(51) Int. Cl.
*A61F 2/06* (2006.01)
(52) U.S. Cl. ...................................... 623/1.15
(58) Field of Classification Search ............... 623/1.15, 623/1.16, 1.17, 1.2; 606/191–198
See application file for complete search history.

(56) References Cited

U.S. PATENT DOCUMENTS

| | | | | |
|---|---|---|---|---|
| 5,161,547 A | * | 11/1992 | Tower | 606/198 |
| 5,741,327 A | | 4/1998 | Frantzend | 623/1 |
| 5,843,168 A | * | 12/1998 | Dang | 623/1.15 |
| 5,902,475 A | | 5/1999 | Trozera et al. | 205/655 |
| 5,968,093 A | * | 10/1999 | Kranz | 623/1.15 |
| 6,096,072 A | * | 8/2000 | Kanesaka et al. | 623/1.15 |
| 6,171,334 B1 | * | 1/2001 | Cox | 623/1.15 |
| 6,190,403 B1 | * | 2/2001 | Fischell et al. | 623/1.16 |
| 6,251,134 B1 | | 6/2001 | Alt et al. | 623/1.16 |

FOREIGN PATENT DOCUMENTS

| | | |
|---|---|---|
| DE | 199 50 756 A1 | 8/2000 |
| EP | 0 800 801 A1 | 10/1997 |
| EP | 0 864 302 A2 | 9/1998 |
| WO | 97/25937 | 7/1997 |
| WO | 97/26840 | 7/1997 |
| WO | 99/65421 | 12/1999 |
| WO | 00/15151 | 3/2000 |

OTHER PUBLICATIONS

U.S. Appl. No. 10/160,531, filed May 31, 2002, Brown et al.
U.S. Appl. No. 09/426,479, filed Oct. 26, 1999, Brown et al.

* cited by examiner

*Primary Examiner*—Kevin T Truong
(74) *Attorney, Agent, or Firm*—Vidas, Arrett & Steinkraus

(57) ABSTRACT

A flexible tubular stent including loosely interlocked annular elements without intersections or cross-over points.

5 Claims, 4 Drawing Sheets

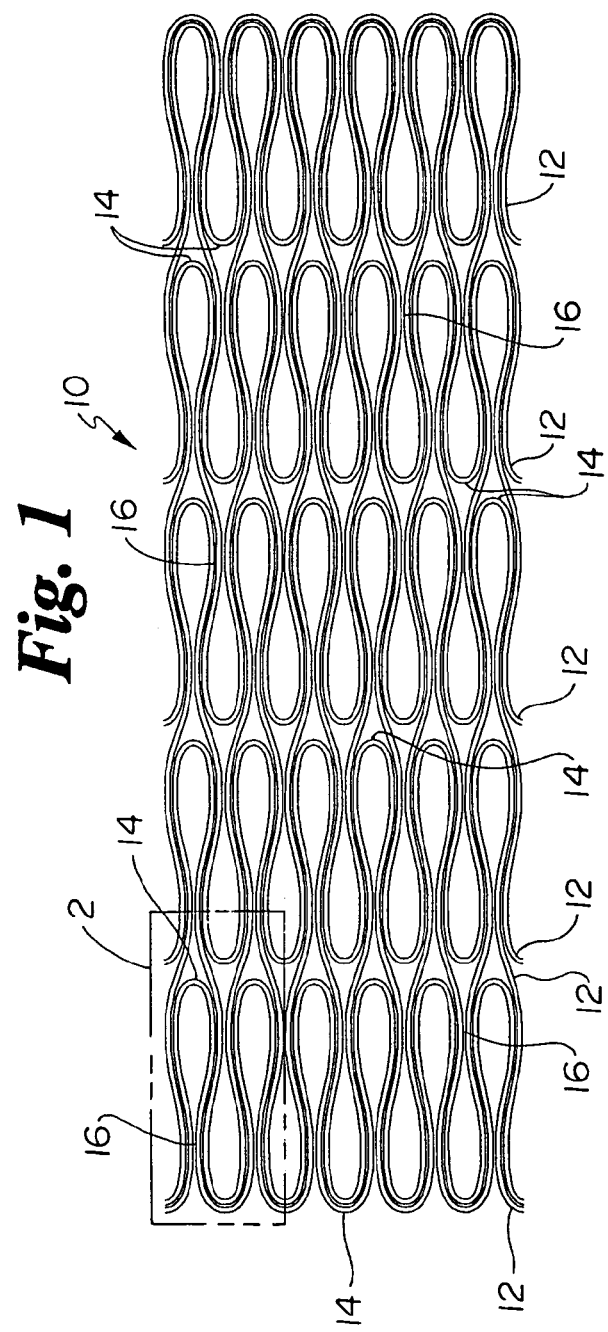
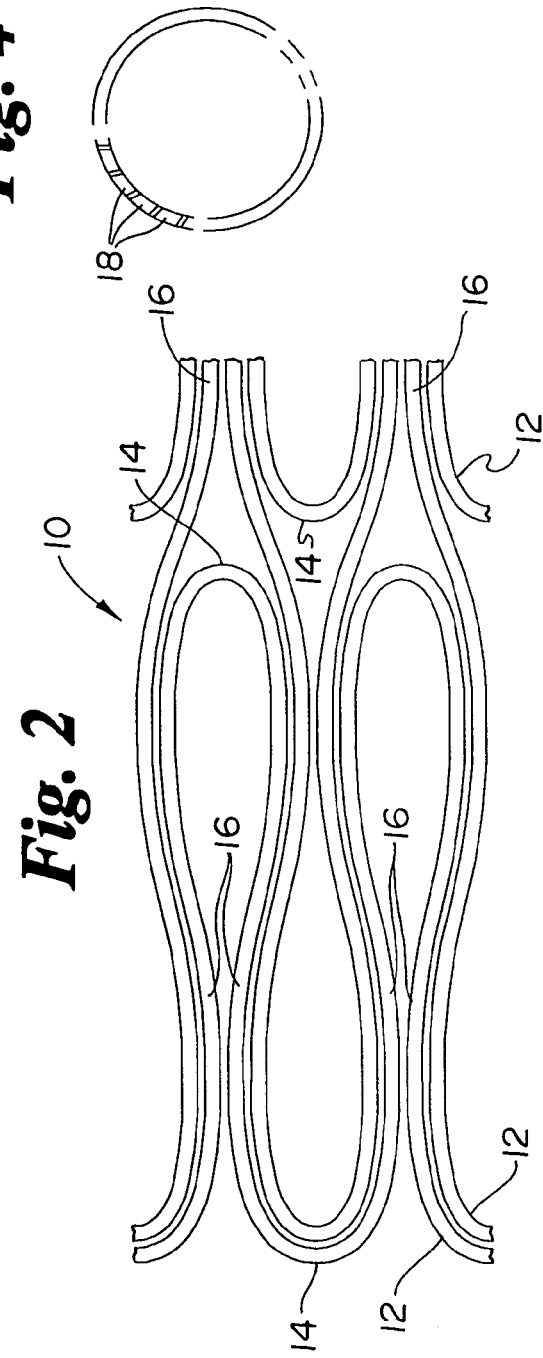
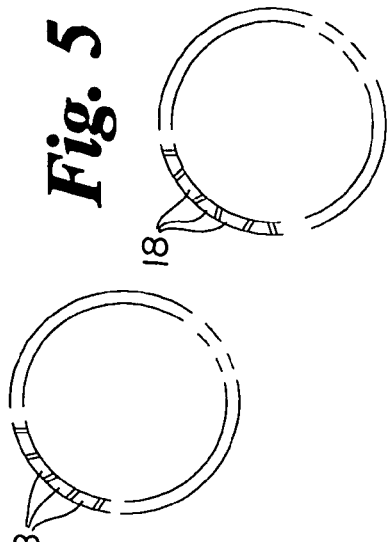

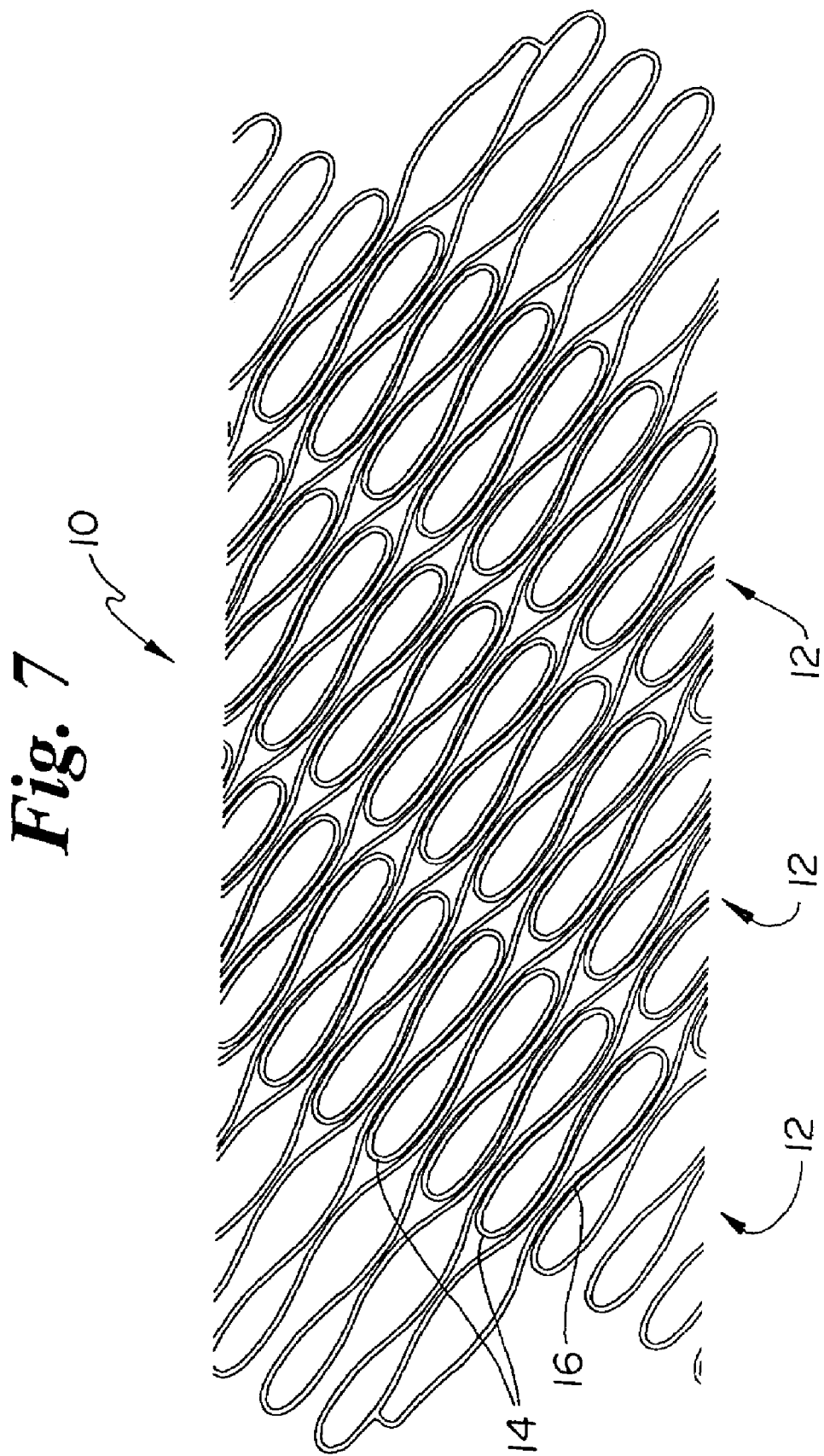

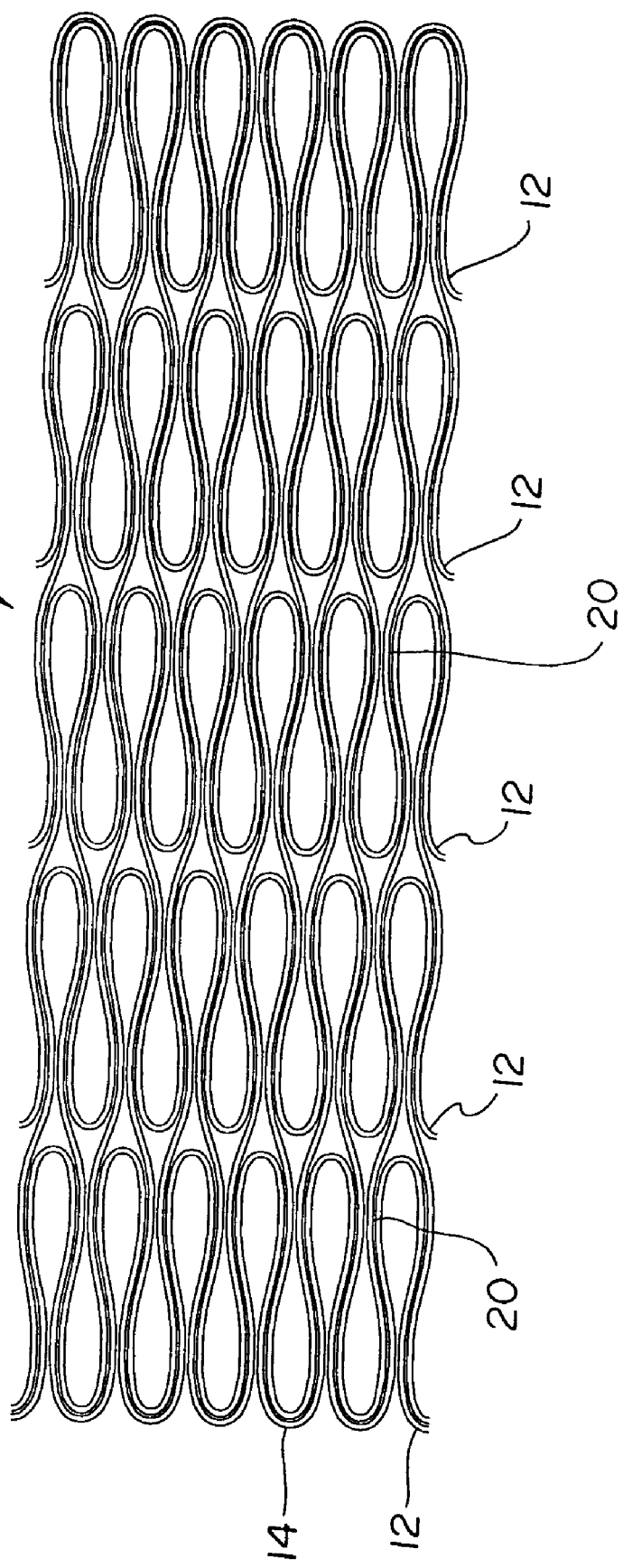

FLEXIBLE STENT

CROSS-REFERENCE TO RELATED APPLICATIONS

This application is a Continuation of U.S. application Ser. No. 10/160,531 filed May 31, 2002 which is a continuation of U.S. application Ser. No. 09/426,479 filed Oct. 26, 1999 (now U.S. Pat. No. 6,409,753), the contents of which are hereby incorporated by reference in their entirety.

BACKGROUND OF THE INVENTION

This invention relates to stents which are implanted in the body.

Stents are used in body lumens, such as blood vessels to maintain them in an open condition. Typically, the stent is delivered into the lumen by a catheter that supports the stent in a compact form during percutaneous insertion and transport through a lumen, such as a vessel, to the desired implantation site. Upon reaching the site the stent is expanded so that it engages the interior wall of the vessel. The catheter is then removed, leaving the stent in the body.

The expansion of the stent may involve forcing it to expand radially outwardly as by inflation of a balloon carried by the catheter or the stent may be of a self-expanding type, several of which are known in the art. For example, the stent may be made of a memory metal such as NITINOL which self-expands in selected temperature ranges.

It can be readily seen that the more flexible the stent is during percutaneous insertion the more easily it can negotiate bends and curves in the lumen or vessel to reach the implantation site.

SUMMARY OF THE INVENTION

This invention provides a stent design of individual annular elements shaped so as to loosely interfit or interlock together with or without intersection and without cross-over points whereby the stent exhibits unusual flexibility.

Preferably, the annular elements are multiple independent serpentine-like rings adjacent to each other having laterally spaced segments 180° out of phase with each other to provide a stepped sequence around each ring, each segment having a wide and a narrow intermediate portion with one set of segments on one side being fitted into an adjacent set of segments on one side of an adjacent serpentine ring to interlock the rings together against longitudinal separation thus forming a flexible cylindrical or tubular structure.

In another aspect of the invention, the edges of the annular rings may be formed at an angle with respect to the center line of the tubular stent configuration rather than aligned therewith as in the prior art. By fabricating the stent with such angular side walls "off center" the rings will interlock with one another against radial separation if moved radially in or out with respect to the stent centerline.

BRIEF DESCRIPTION OF THE DRAWING

FIG. 1 is an unrolled flattened plan of a stent according to a preferred form of the invention;

FIG. 2 is an enlarged portion of FIG. 1 showing in detail the loosely interlocked serpentine rings;

FIGS. 4 and 5 are end views of a stent showing their cylindrical construction and the unique cross-sectional shapes of the struts;

FIGS. 7 and 8 show portions of stents of different embodiments according to this invention.

DESCRIPTION OF THE PREFERRED EMBODIMENTS

Figure 3:
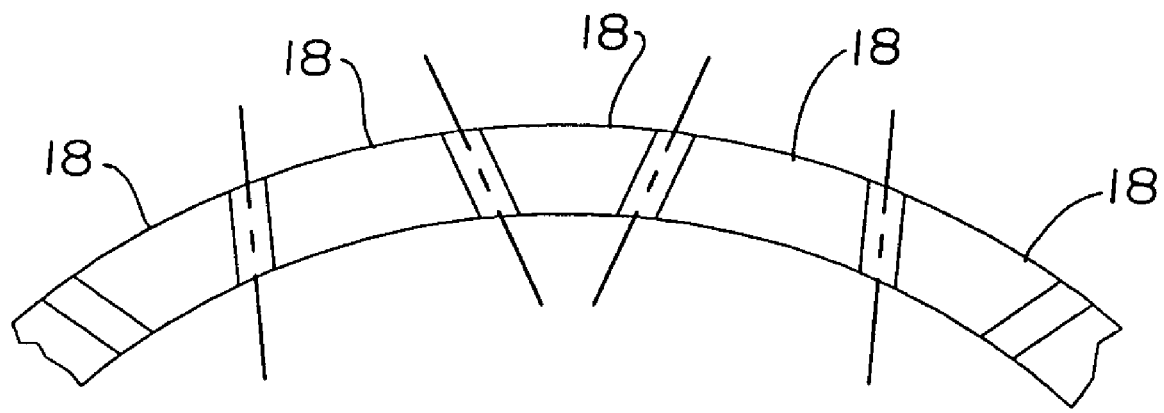
FIG. 3 is an enlarged fragmentary showing of a form of the invention having segments with angular side walls.

Referring to FIGS. 1 and 2, an embodiment of a stent according to the invention is shown and generally designated at 10. Stent 10 is of cylindrical or tubular configuration as can be seen in end view FIGS. 4 and 5 and includes a plurality of annular serpentine segments 12 interfitted with each other over the length of the stent body.

Each annular segment 12 is of a generally serpentine configuration having wide lateral end portions 14 and narrow lateral portions 16 spaced from ends 14, the wide portions of one ring being interfitted into the wide portion of an adjacent ring as shown to prevent longitudinal separation of the serpentine rings. Radial separation of the rings is prevented during handling and delivery by carrying the interfitted rings on a shaft (not shown) as may be provided by the delivery catheter per se.

The stents of the invention may be made of wire or the like. More preferably, they are laser cut from a metal cylinder to a desired configuration.

Historically stents have been constructed of struts with either round, square, trapezoidal, oblong, or other cross-sections. The cross-section of the strut has remained relatively constant throughout the stent. The shape of the strut has been dictated by the starting material, the cutting or shaping process, and the surface finish process. Stent designers can select from a variety of shapes to give the stent unique mechanical properties, but the stent contains the same general cross-section throughout, i.e., if the strut is oblong in shape it remains oblong, if the strut is wider on the OD than the ID it retains this profile throughout the stent. This remains true even if the cross-sectional area of the strut varies in regions of the stent.

A further improvement is shown in FIGS. 3, 4 and 5 in which segments 18 may be formed from a tube or sheet having the side walls "off center" with respect to the center line of the stent so that the segments interlock with one another if moved radially in or out. Two options are shown. FIG. 4 shows the struts laser cut off axis of the center of the stent all in the same direction. FIG. 5 shows a second option in which the off-axis direction of cut alternates around the stent.

The result is a stent which contains elements having multiple varied strut cross-sectional shapes in a predetermined manner. This attribute is desirable because each cross-sectional shape is selected to give the stent unique mechanical properties at that specific location within the stent. By either using a means to selectively remove material or mechanically deform the material, the stent struts can be formed into a tailored shape at selected locations. These tailored shapes can cause the struts to be stronger, weaker, remain flat during expansion, twist during expansion, etc.

Also, varying the cross-section of the stent struts can improve the nesting or the compaction of the struts in the compressed state. By improving the compaction properties of the stent, the stent can achieve lower profiles. There can even be overlapping regions of the various struts without actually causing struts to be deformed into the ID or OD of the stent.

Figure 6:
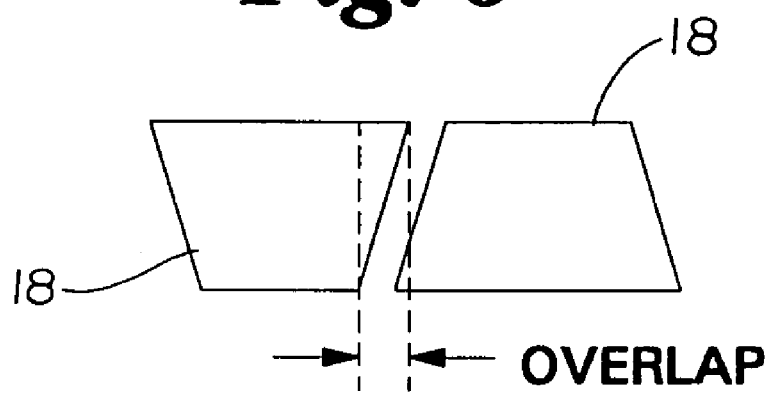
FIG. 6 shows overlap in stent struts.

This helps to maintain a low profile. Additionally, the overlapping of the struts creates a securement means. Each row of struts will help to contain an adjacent row. This is shown in FIG. 6.

Referring now to FIG. 7, there is shown an example of a stent 10 in fragment to illustrate that a stent according to the invention may be made of a single elongated piece of wire or the like.

In FIG. 8, interconnections 20 are shown between rings 12 in a stent 10, showing in plan.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. A flexible expandable stent comprising a plurality of serpentine structures loosely interfitted in mated relationship with adjacent serpentine structures to form a cylindrical stent body, the serpentine structures comprising a plurality of segments including wide and narrow portions, the wide portions of the serpentine structures being interfitted into the wide portions of the adjacent serpentine structures, the serpentine structures disposed helically about the stent body.

2. The stent of claim 1 in which the serpentine structures are formed of material having substantially flat sides.

3. The stent of claim 1 cut from a metal tube whereby a plurality of substantially flat sided struts in cross-section are provided.

4. The stent of claim 3 in which edges of at least some of the struts are angled with respect to the edges of adjacent struts whereby radial separation is prevented.

5. The stent of claim 1 formed of a single piece of wire.

* * * * *